US011504045B2

United States Patent
Bae et al.

(10) Patent No.: US 11,504,045 B2
(45) Date of Patent: Nov. 22, 2022

(54) APPARATUS AND METHOD FOR DETECTING QRS OF ECG

(71) Applicant: Electronics and Telecommunications Research Institute, Daejeon (KR)

(72) Inventors: Tae Wuk Bae, Daegu (KR); Kee Koo Kwon, Daegu (KR); Kyu Hyung Kim, Daegu (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 0 days.

(21) Appl. No.: 17/103,665

(22) Filed: Nov. 24, 2020

(65) Prior Publication Data

US 2021/0153763 A1 May 27, 2021

(30) Foreign Application Priority Data

Nov. 25, 2019 (KR) .................. 10-2019-0152782

(51) Int. Cl.
  *A61B 5/316* (2021.01)
  *A61B 5/352* (2021.01)
(52) U.S. Cl.
  CPC .............. *A61B 5/316* (2021.01); *A61B 5/352* (2021.01)
(58) Field of Classification Search
  None
  See application file for complete search history.

(56) References Cited

U.S. PATENT DOCUMENTS

| 9,814,405 | B2* | 11/2017 | Yang | A61B 5/7232 |
|---|---|---|---|---|
| 2010/0014773 | A1* | 1/2010 | Ito | H04N 5/20 382/266 |
| 2013/0150741 | A1 | 6/2013 | Noh et al. | |
| 2015/0105679 | A1 | 4/2015 | Hwang | |
| 2016/0045117 | A1* | 2/2016 | Liu | A61B 5/7221 600/502 |
| 2019/0336026 | A1* | 11/2019 | Dawoud | A61N 1/3756 |
| 2019/0336083 | A1* | 11/2019 | Gill | A61B 5/7217 |

FOREIGN PATENT DOCUMENTS

| KR | 1020130030245 A | 3/2013 |
|---|---|---|
| KR | 101524596 B1 | 6/2015 |

* cited by examiner

*Primary Examiner* — Catherine M Voorhees
*Assistant Examiner* — Roland Dinga
(74) *Attorney, Agent, or Firm* — William Park & Associates Ltd.

(57) ABSTRACT

Provided are an apparatus and method for detecting ventricular depolarization (QRS) of an electrocardiogram (ECG). The apparatus includes an input unit configured to receive an ECG signal, a memory configured to store a program for detecting R and ventricular depolarization using the ECG signal, and a processor configured to execute the program, wherein the processor detects a QRS interval and an R-peak using a first-order derivative filter and a max-filter.

6 Claims, 19 Drawing Sheets

APPARATUS AND METHOD FOR DETECTING QRS OF ECG

CROSS-REFERENCE TO RELATED APPLICATION

This application claims priority to and the benefit of Korean Patent Application No. 10-2019-0152782, filed on Nov. 25, 2019, the disclosure of which is incorporated herein by reference in its entirety.

BACKGROUND

1. Field of the Invention

The present invention relates to an apparatus and method for detecting ventricular depolarization (QRS) of an electrocardiogram (ECG).

2. Discussion of Related Art

Cardiac arrhythmia refers to a group of conditions that cause the heart to beat too quickly (more than 100 beats per minute in adults) or too slowly (less than 60 beats per minute).

Arrhythmia is usually asymptomatic, but in severe cases, it can cause dizziness, fainting, shortness of breath, or chest pain, and in particularly severe cases it can lead to a risk of cardiac arrest.

The R-R (R-peak interval) detection technique according to the conventional art is not suitable for real-time processing due to a large amount of computation, and detection techniques with a small amount of computation contain many errors and poor analysis reliability due to insufficient coping with noise.

SUMMARY OF THE INVENTION

The present invention is proposed to solve the above-described problems and is directed to providing an apparatus (e.g., a portable ECG apparatus) and method capable of efficiently detecting R and QRS in real time using a pair of derivative filters and a max filter.

According to an aspect of the present invention, there is provided an apparatus for detecting ventricular depolarization of an electrocardiogram (ECG), the apparatus including an input unit configured to receive an ECG signal, a memory configured to store a program for detecting R and ventricular depolarization using the ECG signal, and a processor configured to execute the program, wherein the processor detects a QRS interval and an R-peak using a first-order derivative filter and a max-filter.

According to another aspect of the present invention, there is provided a method of detecting ventricular depolarization, the method including detecting a QRS interval and an R-peak by applying a pair of derivative filters and a max-filter to a received ECG signal, detecting a noise interval and detecting an R-peak in the noise interval, and setting a candidate of an R-R interval and modifying the R-R interval in consideration of noise.

According to another aspect of the present invention, there is provided an apparatus for detecting ventricular depolarization of an electrocardiogram (ECG), the apparatus including an R-point detection module configured to detect an R-peak in a QRS interval using an ECG signal, a noise detection module configured to detect a noise interval and an R-peak in the noise interval, and an R-R interval modification module configured to modify an R-R interval using detection results of the R-point detection module and the noise detection module and then analyze heart rate variability.

DETAILED DESCRIPTION OF EXEMPLARY EMBODIMENTS

These and other objects, advantages, and features of the present invention, and implementation methods thereof will be clarified through the following embodiments described with reference to the accompanying drawings.

The present invention may, however, be embodied in different forms and should not be construed as being limited to the embodiments set forth herein. Rather, these embodiments are provided so that this disclosure will fully convey the objects, configurations, and effects of the present invention to those skilled in the art. The scope of the present invention is defined solely by the appended claims.

The terminology used herein is for the purpose of describing particular embodiments only and is not intended to be limiting to the invention. As used herein, the singular forms "a," "an," and "one" include the plural unless the context clearly indicates otherwise. The terms "comprises" and/or "comprising," when used in this specification, specify the presence of stated elements, steps, operations, and/or components, but do not preclude the presence or addition of one or more other elements, steps, operations, and/or components.

Hereinafter, in order to help those skilled in the art to understand the present invention, the background of the present invention will be described first, and then the embodiments of the present invention will be described.

Cardiac arrhythmia refers to a group of conditions that cause the heart to beat too quickly (more than 100 beats per minute in adults) or too slowly (less than 60 beats per minute).

Arrhythmia is usually asymptomatic, but in severe cases, it can cause dizziness, fainting, shortness of breath, or chest pain, and in particularly severe cases it can lead to a risk of cardiac arrest.

Figure 1:
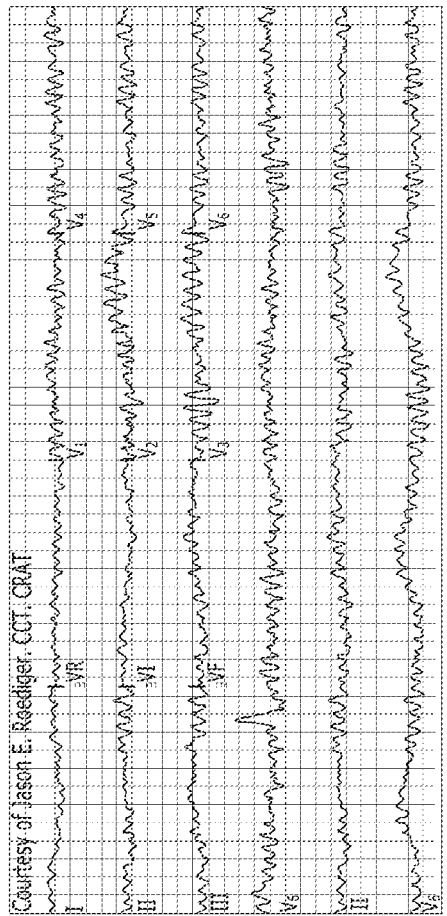
FIG. 1 shows arrhythmic waveforms.
Figure 2:
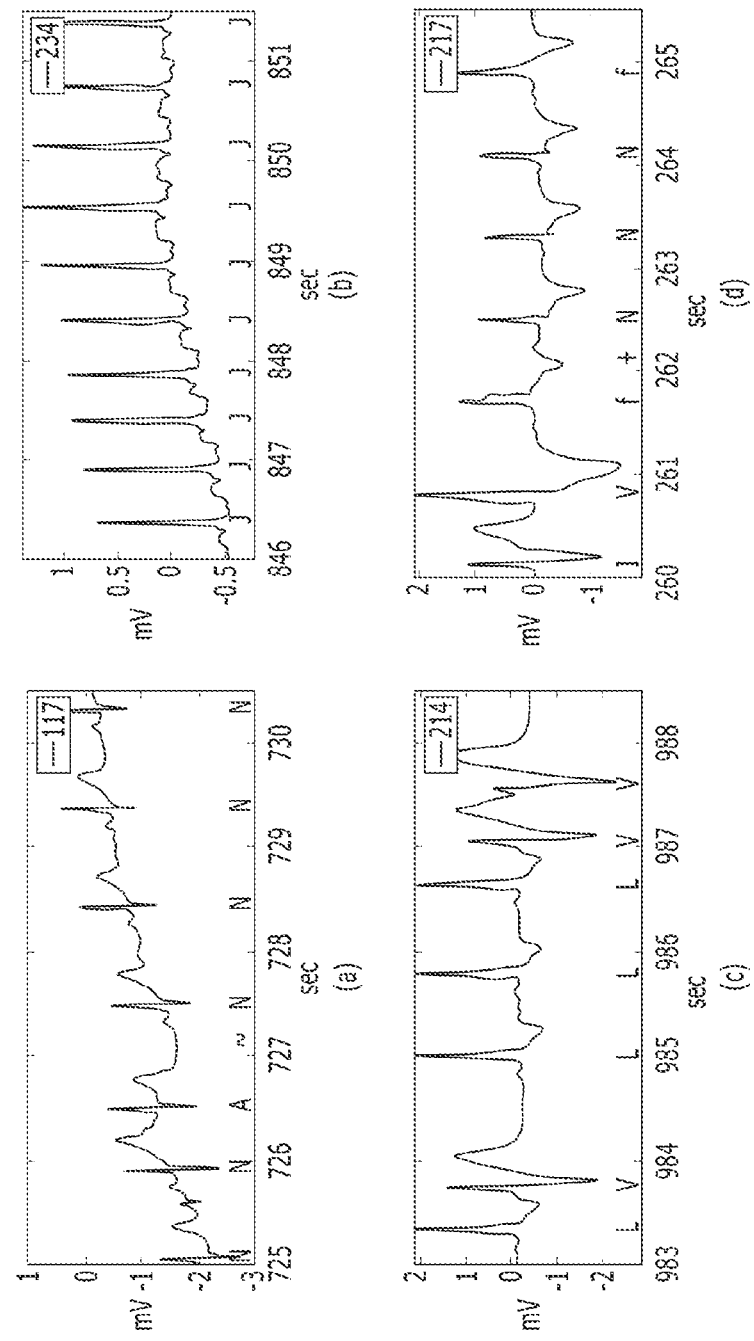
FIG. 2 shows a representative example of arrhythmic waveforms.

As shown in FIG. 2, representative aspects of an electrocardiogram (ECG) arrhythmia include an atrial premature beat (shown as A in FIG. 2), a junctional premature beat (shown as J in FIG. 2), a premature ventricular contraction (shown as V in FIG. 2), and atrial fibrillation, and the ECG arrhythmia is characterized by a very unstable heart rate.

According to the conventional art, in order to detect an R-R interval, which is the basis for arrhythmia research, a detection technique based on a transform (a wavelet transform, the Hilbert transform, etc,), a detection technique based on a filter (Kalman filter, an intermediate band filter, a filter bank), and a neural-network-based detection technique, a threshold-based detection technique, and the like have been proposed. Most of the R-R detection techniques have difficulty in real-time processing because of a large amount of computation, and threshold-based detection techniques with a low amount of computation cause many errors in R-R detection.

Also, the threshold-based detection techniques have low reliability of ECG analysis due to insufficient coping with noise.

To solve the above-described problems, the present invention proposes a method of efficiently detecting R and QRS in real time using a pair of derivative filters and a max-filter in order to analyze an ECG signal measured by a wearable ECG device in real time.

According to an embodiment of the present invention, by notifying a hospital (or a doctor) or a patient with arrhythmia or suspected arrhythmia of the patient's electrocardiogram status, it is possible to prevent a heart disease incident.

Figure 3:
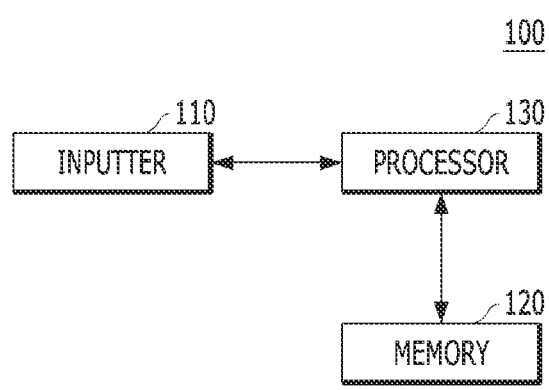
FIG. 3 shows an apparatus for detecting ventricular depolarization of an electrocardiogram according to an embodiment of the present invention.

FIG. 3 shows an apparatus for detecting ventricular depolarization of an electrocardiogram according to an embodiment of the present invention.

An apparatus 100 for detecting ventricular depolarization of an electrocardiogram (ECG) according to an embodiment of the present invention includes an input unit 110 configured to receive an ECG signal, a memory 120 configured to store a program for detecting R and ventricular depolarization using the ECG signal, and a processor 130 configured to execute the program. The processor 130 detects a QRS interval and an R-peak using a first-order derivative filter and a max-filter.

The processor 130 detects an R-peak in units of sliding windows, performs real-time processing, and performs connection using R-peaks overlapping between the sliding windows.

The processor 130 classifies a noise region in the ECG signal using a vertical histogram.

The processor 130 detects QRS features using a pair of first-order derivative filters.

The processor 130 detects QRS features by using a result of filtering the ECG signal with a rising derivative filter and a falling derivative filter.

The processor 130 extends a QRS candidate interval by applying the max-filter to the QRS features.

The processor 130 detects a QRS interval in the QRS candidate interval using a threshold.

When a negative peak value is greater than a predetermined multiple of a positive peak value with respect to the average of the sliding window, the processor 130 predicts premature ventricular contraction (PVC) and searches for the position of a corresponding R-peak.

When an R-point is detected in the noise region, the processor 130 excludes preceding and following R-R intervals related to the R-point from analysis.

Figure 4:
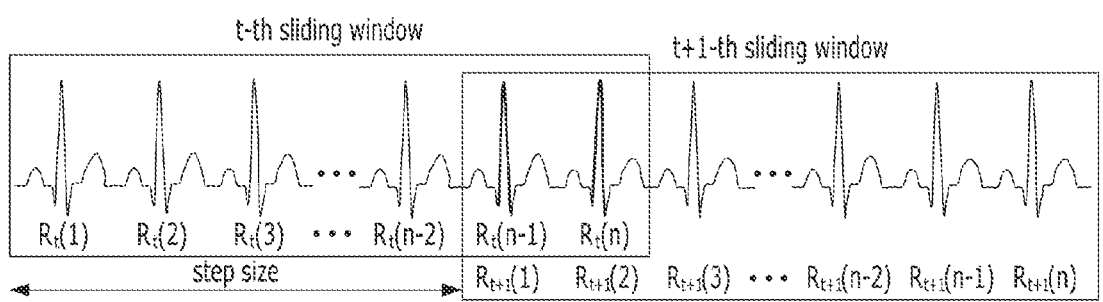
FIG. 4 shows R-peak point connection in a sliding window according to an embodiment of the present invention.

The processor 130 determines whether an initial R in the current sliding window overlaps R in the previous sliding window and excludes an R-R interval lacking continuity between the sliding windows from analysis, FIG. 4 shows R-peak point connection in a sliding window according to an embodiment of the present invention.

As shown in FIG. 4, a processor according to an embodiment of the present invention detects R-peaks in units of sliding windows in order to perform real-time processing.

Subsequently, in order to merge the R-peaks detected in the slide windows, the processor detects an R-peak (a red portion shown in FIG. 4) overlapping between the sliding windows and connects R-peaks detected in the preceding and following sliding windows using the detected overlapping R-peak.

Figure 5:
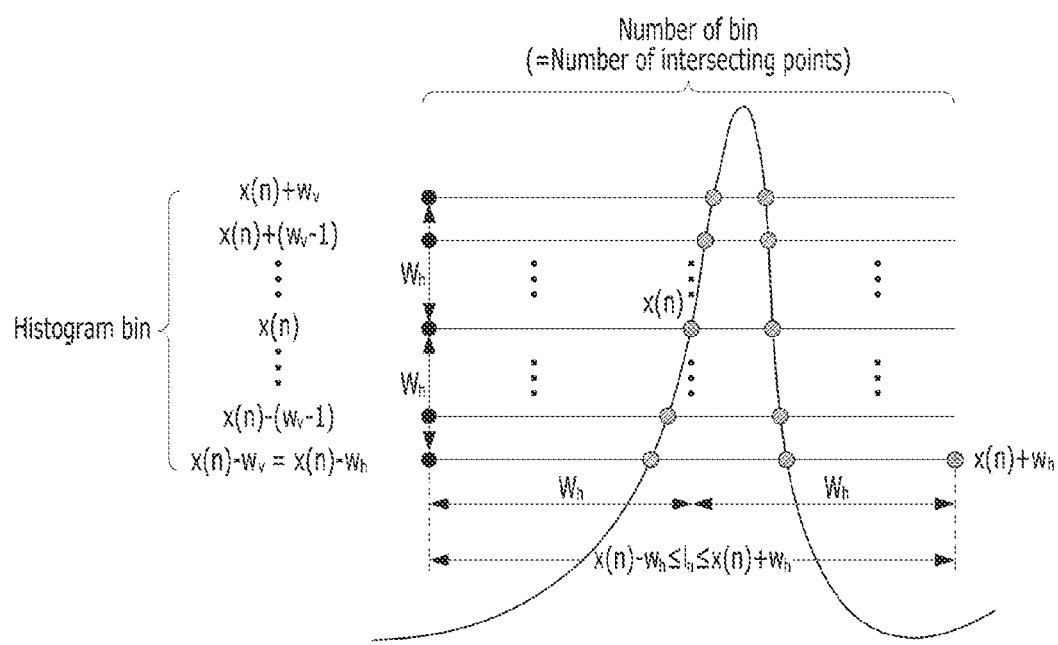
FIG. 5 shows a vertical histogram for a region of interest (ROI) of a signal point according to an embodiment of the present invention.

FIG. 5 shows a vertical histogram for a region of interest (ROI) of a signal point according to an embodiment of the present invention.

Since according to an embodiment of the present invention, it is possible to increase robustness against baseline wandering (BW) by processing a sliding window unit and a derivative filter, the noise detection design is characterized by the detection of root noise.

A vertical history in an ROI around a signal point for detecting root noise is as shown in FIG. 5.

The total number of bins is $2 \times W_v + 1$, and a histogram sum h(n) for x(n) with histogram $m_i$ is expressed as Equation 1.

$$h(n) = \sum_{i=x(n)-W_v}^{x(n)+W_v} m_i \qquad \text{[Equation 1]}$$

where $W_v = 15$. In the histogram for x(n), the total number of bins is always constant, but the range of the bin value varies depending on the signal size of x(n).

Also, the histogram $m_i$ indicates the number of bin i (a signal magnitude value) for an ECG signal in an ROI, and the histogram value increases in a local region with high frequency, such as root noise.

Figure 6:
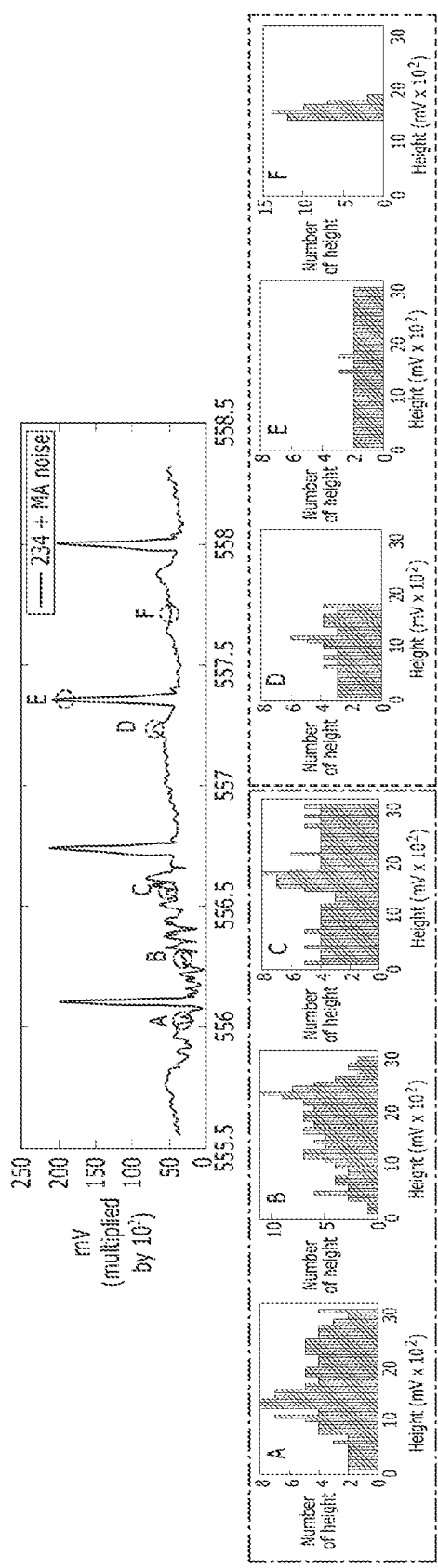
FIG. 6 shows a vertical histogram in a noise region and an ECG signal region according to an embodiment of the present invention.

FIG. 6 shows a vertical histogram in a noise region and an ECG signal region according to an embodiment of the present invention.

As shown in FIG. 6, a noisy signal is created by adding a motion artifact (MA) to Massachusetts Institute of Technology-Beth Israel Hospital (MIT-BIH) signal No. 234.

The vertical histogram value is generally high fir each bin in the noise region, whereas the vertical histogram distribution varies depending on the position of a processed point in the general ECG signal region.

In the case of an ECG signal, a vertical histogram at a peak point of an important wave (D in FIG. 6) is concentrated in a low bin interval.

A rising or falling interval (E in FIG. 6) of the wave has a flat histogram distribution (flat skewness) over the entire bin range, whereas a flat interval (F in FIG. 6) has a histogram distribution (high skewness) concentrated in a specific bin.

As a result, it can be seen that the vertical histogram sum in the noise region is larger than that in the general ECG signal region, and the vertical histogram sum at each signal point is used to distinguish a noise point from a general signal point.

Figure 7:
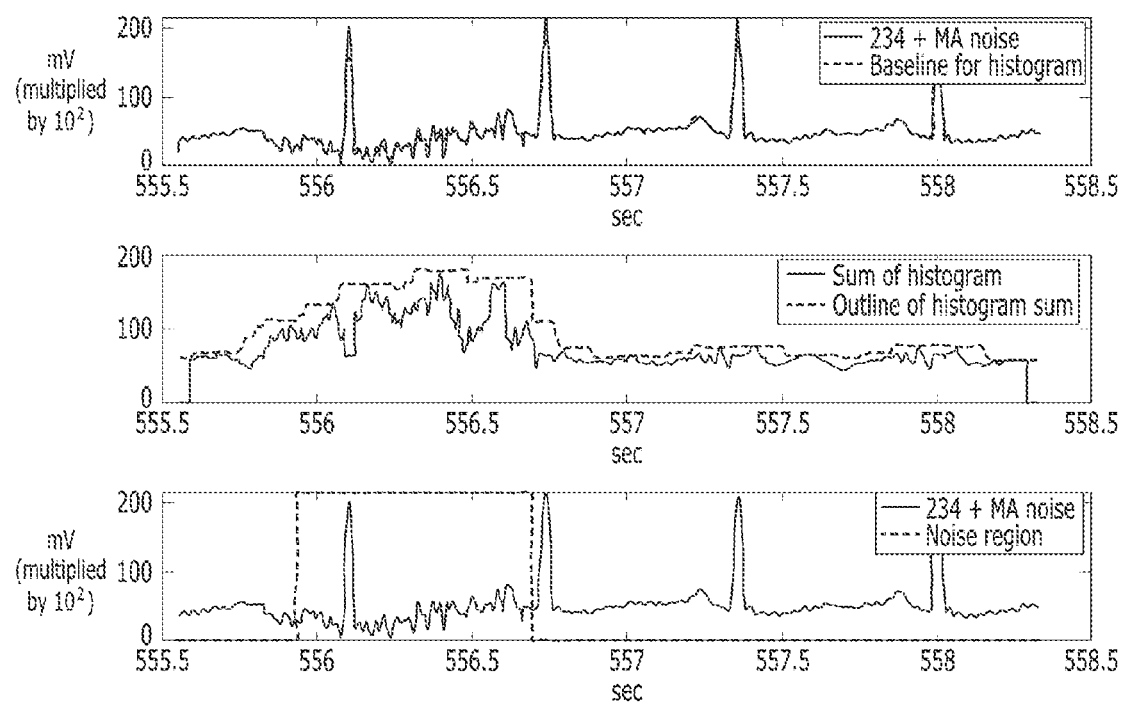
FIG. 7 shows a noise region detected by adding a noise signal, a baseline, and a histogram for each position and applying a max-filter according to an embodiment of the present invention.

FIG. 7 shows a noise region detected by adding a noise signal, a baseline, and a histogram for each position and applying the max-filter according to an embodiment of the present invention.

A result of detecting a noise region using a vertical histogram and a max-filter is as shown in FIG. 7.

A baseline for calculating the vertical histogram is obtained by applying a median filter with a size of 1×10 to a noisy signal.

in the second row of FIG. 7, the outline of the vertical histogram sum is obtained by applying a max-filter with a size of 1×25 to the sum of the vertical histogram two times.

The average of the top 20% and bottom 20% in the outline of the histogram sum is used as an appropriate threshold for detecting a noise interval.

Figure 8:
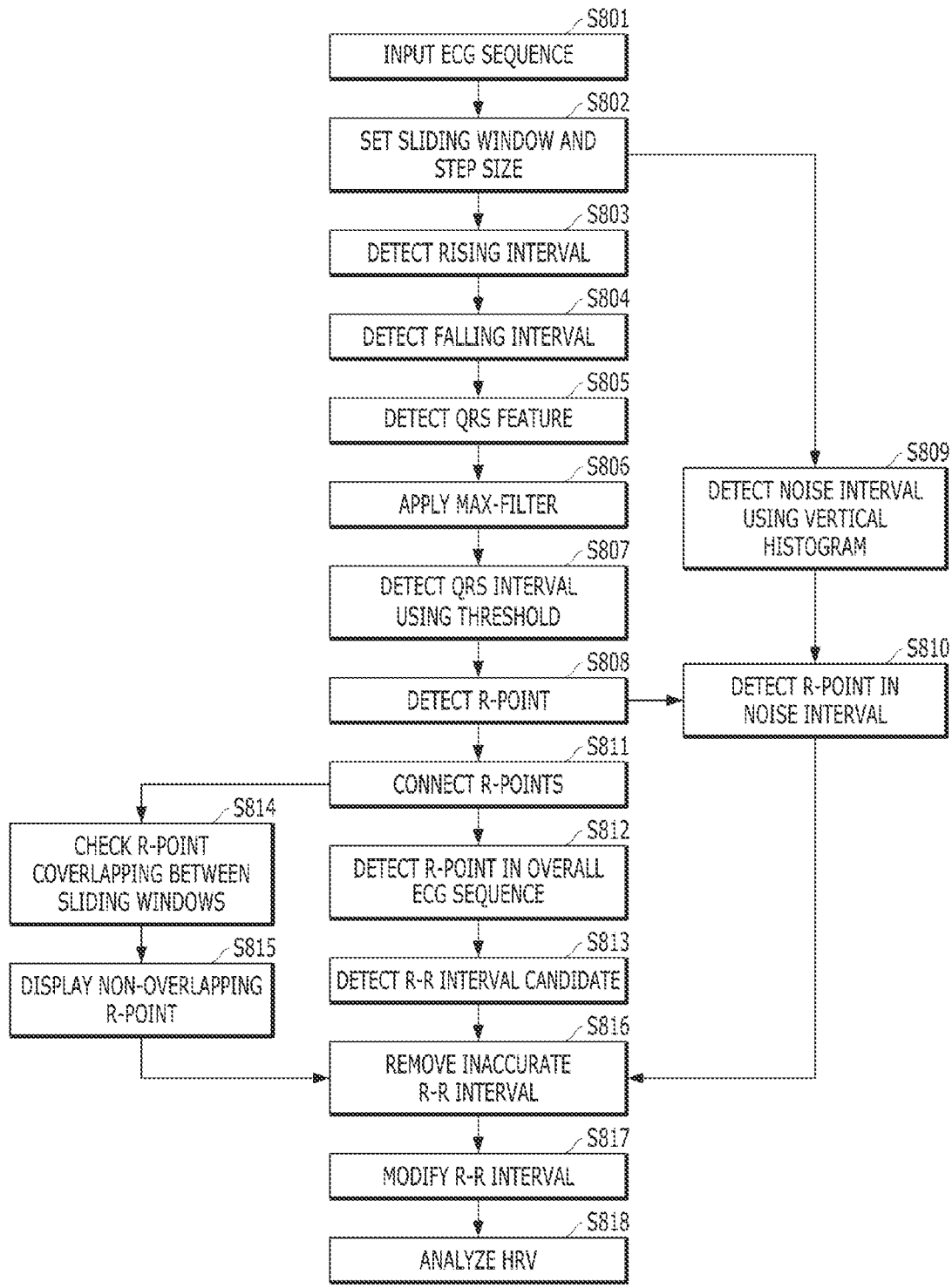
FIG. 8 shows a method of detecting ventricular depolarization of an electrocardiogram according to an embodiment of the present invention.

FIG. 8 shows a method of detecting ventricular depolarization of an electrocardiogram according to an embodiment of the present invention.

The method of detecting ventricular depolarization of an electrocardiogram according to an embodiment of the present invention is performed by an R-point detection module, a noise detection module, and a detected-R-point connection module.

An apparatus for detecting ventricular depolarization of an electrocardiogram according to an embodiment of the present invention includes an R-point detection module configured to detect an R-peak in a QRS interval using an ECG signal, a noise detection module configured to detect a noise interval and an R-peak in the noise interval, and an R-R interval modification module configured to modify an R-R interval using detection results of the R-point detection module and the noise detection module and then analyze heart rate variability.

The R-point detection module detects R-peaks in units of sliding windows, connects R-peaks overlapping between the sliding windows, acquires a QRS candidate interval using a pair of first-order derivative filters, a max-filter, and a threshold, and detects an R-peak in the QRS candidate interval.

The noise detection module detects a noise interval using a vertical histogram value. The R-R interval modification module modifies an R-R interval by excluding an R-R interval related to an R-peak detected in the noise interval from analysis and excluding an R-R interval lacking continuity from the analysis according to a result of determining whether an R-peak overlaps between sliding windows.

A method of detecting ventricular depolarization of an electrocardiogram (ECG) according to an embodiment of the present invention includes (a) detecting a QRS interval and an R-peak by applying a pair of derivative filters and a max-filter to a received ECG signal, (b) detecting a noise interval and detecting an R-peak in the noise interval, and (c) setting a candidate of R-R interval and modifying the R-R interval in consideration of noise.

Operation (a) includes detecting a QRS feature using a pair of first-order derivative filters for a rising derivative filter acid a falling derivative filter.

Operation (a) includes detecting a QRS feature by multiplying a result of applying the pair of first-order derivative filters.

Operation (a) includes extending a QRS candidate interval by applying a max-filter, and detecting a QRS interval using a threshold.

Operation (a) includes detecting an R-peak in the QRS candidate interval and predicting PVC and searching for the position of a corresponding R-peak when a negative peak value is greater than a predetermined multiple of a positive peak value on the basis of the average of a sliding window.

Operation (b) includes classifying a noise region in the ECG signal using a vertical histogram.

Operation (c) includes excluding preceding and following R-R intervals related to the R-peak detected in the noise region from analysis.

Operation (c) includes determining whether an initial R in the current sliding window overlaps R in the previous sliding window and excluding an R-R section lacking continuity between the sliding windows from analysis.

Referring to FIG. 8, when an ECG sequence is input in S801, a sliding window and a step size are set in S802.

According to an embodiment of the present invention, an R-peak is detected using a pair of first-order derivative filters [−1, 1] and [1, −1].

A derivative filter RDF [−1, 1] detects a steeply rising curve of QRS in S803 whereas a derivative filter DDF [1, −1] detects a rapidly falling curve of QRS in S804.

In S805, a QRS feature is detected using the product of the filtering results of the derivative filters.

In this case, the product of the derivative filter results improves the QRS interval but suppresses P-wave or T-wave and noise.

A max-filter is applied to the product of the derivative filter results in S806, and a QRS interval and an R-peak are detected through normalization and a threshold in S807 and S808.

Figure 9:
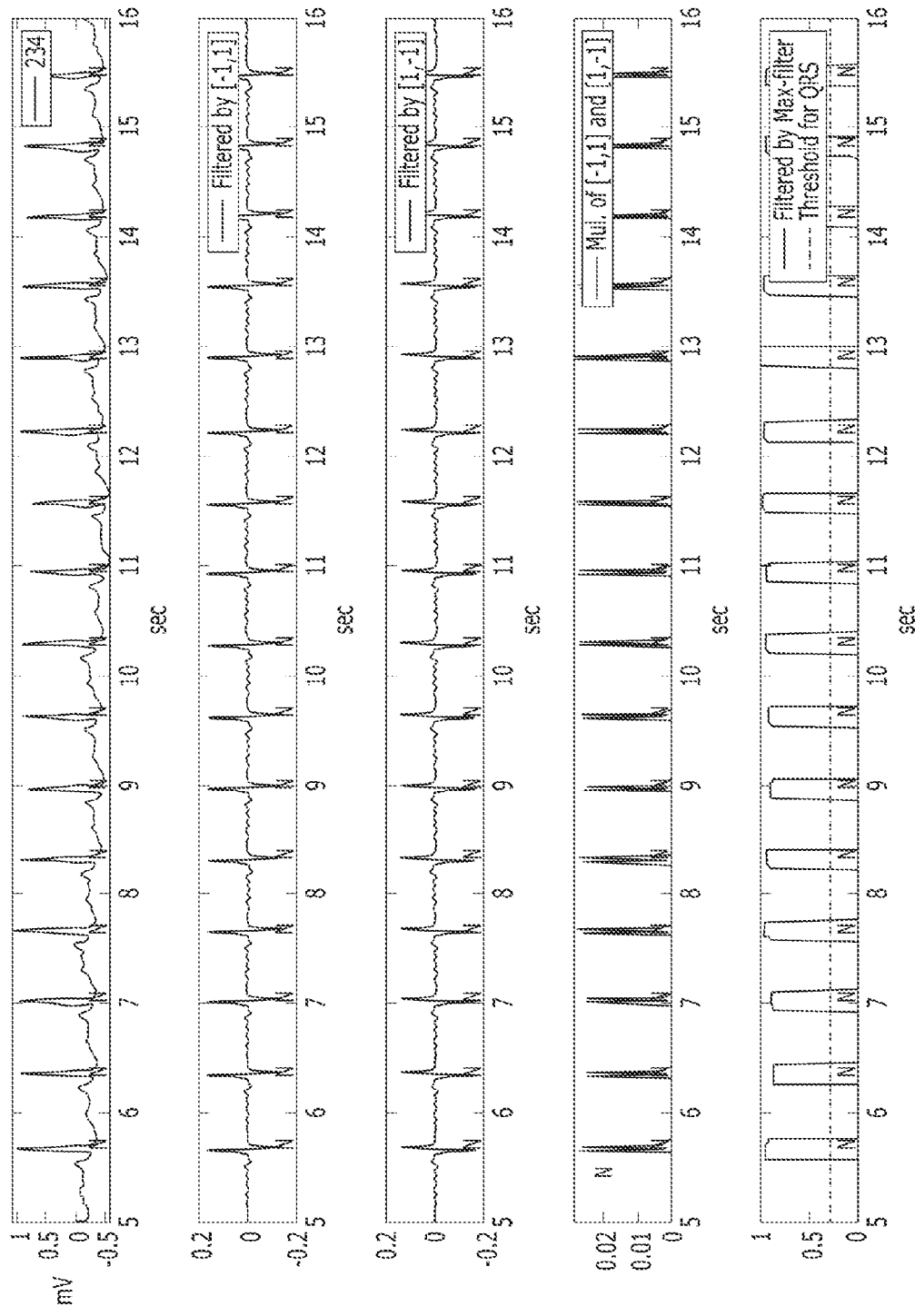
FIG. 9 shows an example of QRS detection for record 234 of the Massachusetts Institute of Technology-Beth Israel Hospital (MIT-BM_arrhythmia database according to an embodiment of the present invention.

FIG. 9 shows an example of QRS detection for record 234 of the MIT-BH arrhythmia database according to an embodiment of the present invention.

FIG. 9 shows an example of a QRS detection procedure using a pair of derivative filters for signal 234 of MIT-BIH.

A QRS interval including an R-peak includes steeply rising and falling intervals compared to other signal intervals.

A derivative filter result $D_\alpha(n)$ for an original ECG signal $I(n)$ with a size equal to a sliding window is obtained as Equation 2.

$$D_\alpha(n) = \Sigma_{k=0}^{2j-1} d_\alpha(k) I(n+k) \qquad \text{[Equation 2]}$$

where $d_\alpha(k)$ is a derivative filter, and j is half of a signal point interval to which a derivative filter is to be applied.

In an embodiment of the present invention, j=1. is used.

$$\begin{cases} d_a(k) = (-1) \times \alpha, & \text{for } 0 \le k < j \\ d_a(k) = 1 \times \alpha, & \text{for } j \le k \le 2j-1 \end{cases} \qquad \text{[Equation 3]}$$

where $\alpha$ is the type of a derivative filter, and $\alpha=1$ and $\alpha=-1$ denote derivative filters that detect a rising interval and a falling section, respectively.

A basic feature of the QRS interval including the steeply rising and falling intervals is acquired by multiplying two types of derivative filter results as expressed in Equation 4 (S805).

$$D(n) = D_{-1}(n) D_1(n) \quad \text{[Equation 4]}$$

In order to integrate the detected rising and falling intervals, a max-filter is applied to the product result of the derivative filters as expressed in Equation 5 below (S806).

$$M(n) = \max_{n-f \le s \le n+f} \{D(s)\} \quad \text{[Equation 5]}$$

where f(=15) is the size of half of the max-filter.

Figure 10:
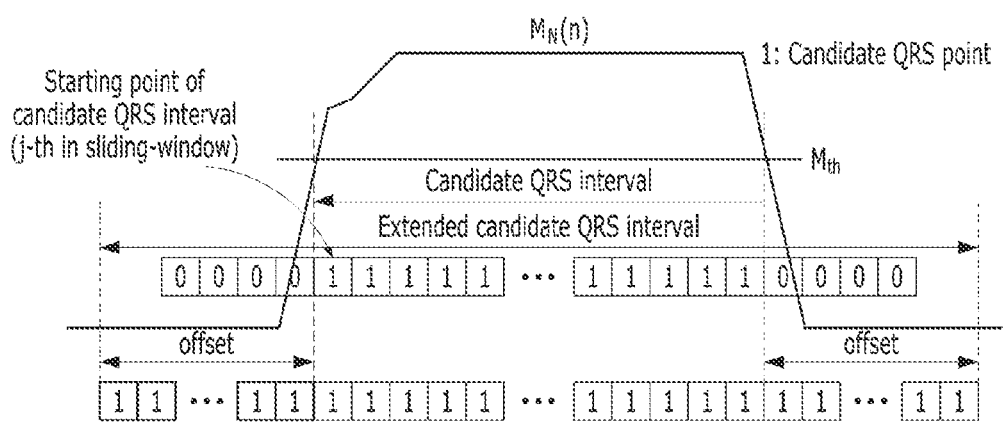
FIG. 10 shows a QRS candidate interval acquired using a max-filter and a threshold according to an embodiment of the present invention.

FIG. 10 shows a candidate QRS interval acquired using a max-filter and a threshold according to an embodiment of the present invention.

As shown in FIG. 10, by applying a threshold to a normalized max-filter result $M_N(n)$, the candidate QRS interval is acquired as expressed in Equation 6 below (S807).

$$I(n) = \begin{cases} \text{candidate } QRS \text{ point}, & \text{if } M_N(n) > M_{th} \\ \text{non-candidate } QRS \text{ point}, & \text{else} \end{cases} \quad \text{[Equation 6]}$$

where $M_{th}$ is a threshold for determining whether the current point belongs to the candidate QRS interval.

When the number of consecutive candidate QRS points ("1" in FIG. 9) exceeds a specific threshold, the interval is classified as a candidate QRS interval including R.

A candidate QRS interval extended to increase the reliability of an R-detection rate is obtained by adding an additional interval to both sides of the candidate QRS interval.

The R-peak position is found in an extracted candidate QRS interval in FIG. 10.

The R-peak detection. method depends on the shape of R-wave and is classified into a normal case and a PVC case.

A normal R-peak shape indicates a high positive R-peak shape, whereas an R-peak shape in PVC appears as a deep negative R-peak point.

Accordingly, an R-peak position in the candidate QRS interval is obtained in consideration of two cases as expressed in Equation 7.

$$r_L = \begin{cases} \underset{1 \le r \le k}{\operatorname{argmin}} C_{x,j,k}, & \text{if } \beta \times (\max(C_{s,j,k}) - \text{mean}(W_s)) < \\ & (\text{mean}(W_z) - \min(C_{s,j,k})) \\ \underset{1 \le r \le k}{\operatorname{argmin}} C_{s,j,k}, & \text{else} \end{cases} \quad \text{[Equation 7]}$$

where $\beta(=2.5)$ is a coefficient for comparing the height of a positive R-peak and the height of a negative R-peak.

In a PVC beat, the difference between the average of the sliding window and the negative R-peak is much greater than the difference between the positive maximum peak and the average of the sliding window.

According to an embodiment of the present invention, PVC is predicted when a negative peak value is β times a positive peak value with respect to the average of the sliding window.

Figure 11:
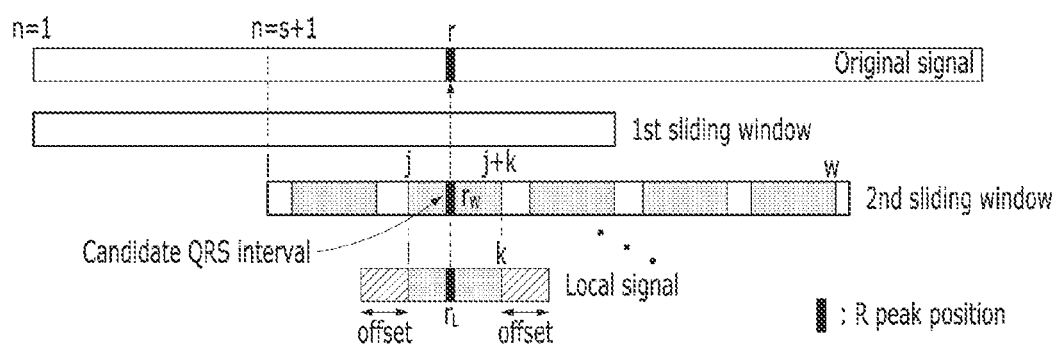
FIG. 11 shows an R-peak position in a sliding window and a local signal according to an embodiment of the present invention.
Figure 12A:
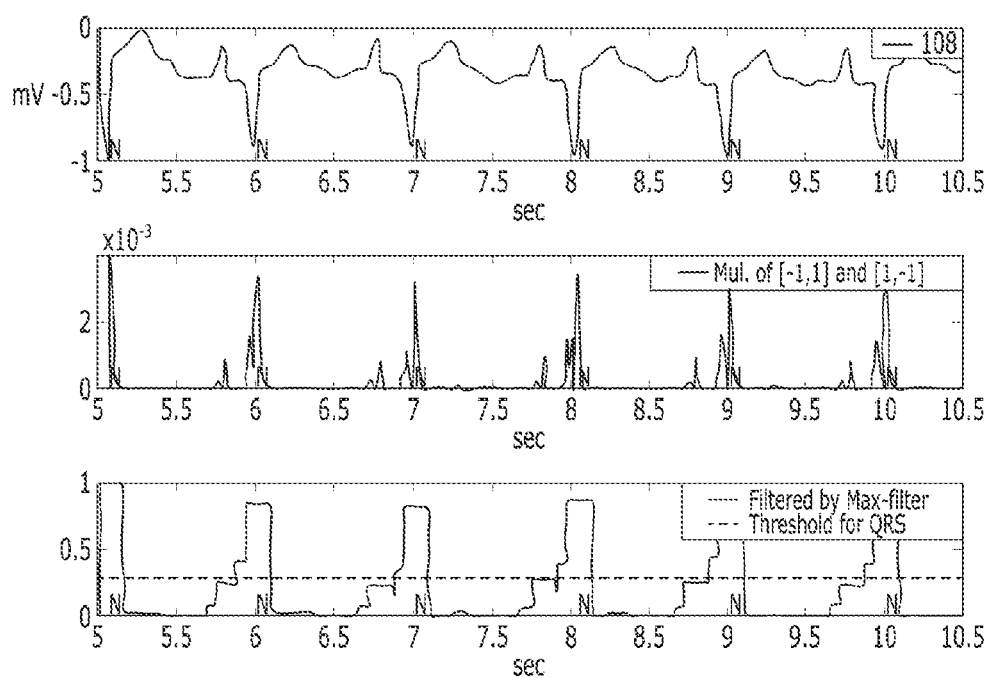
FIG. 12A through FIG. 12E show a QRS detection result for the sections of records 108, 111, 118, 217, and 214 of the MIT-BIH arrhythmia database according to an embodiment of the present invention.
Figure 12B:
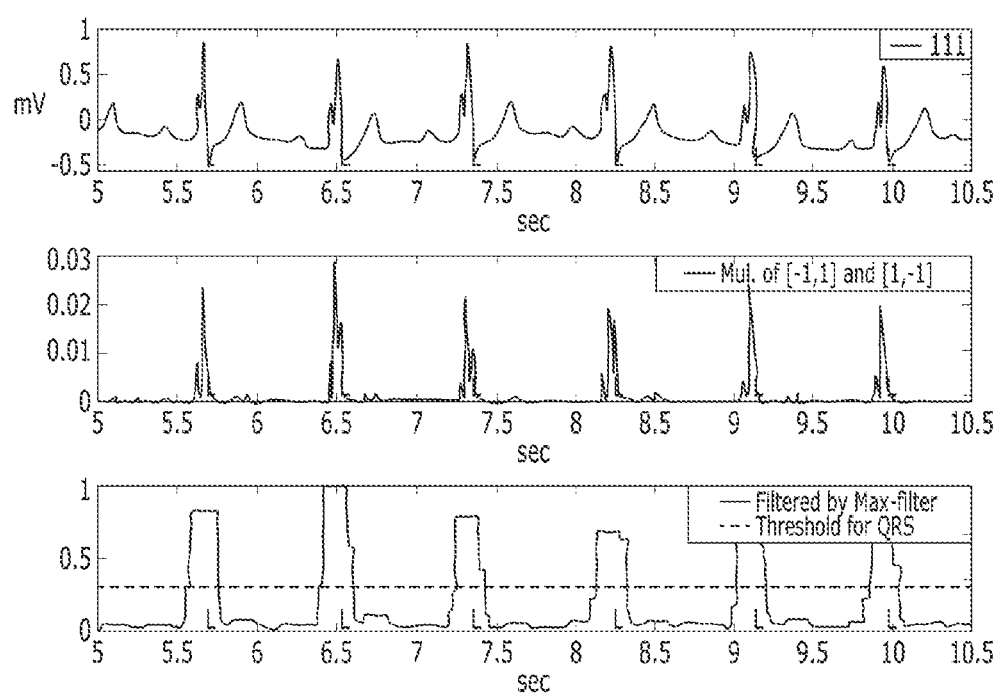
Figure 12C:
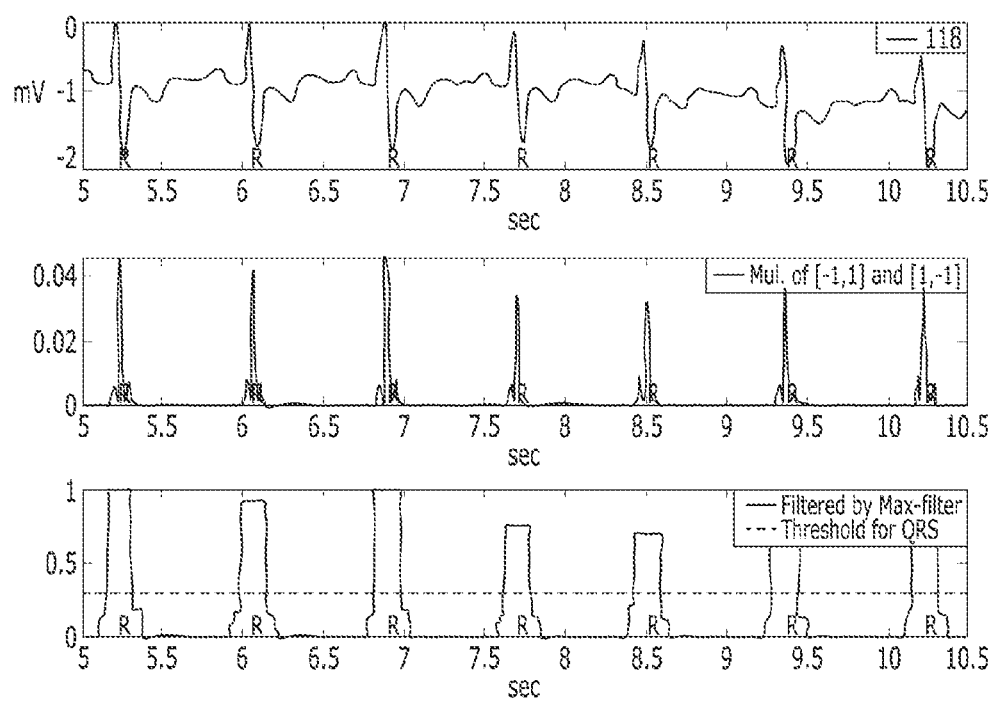
Figure 12D:
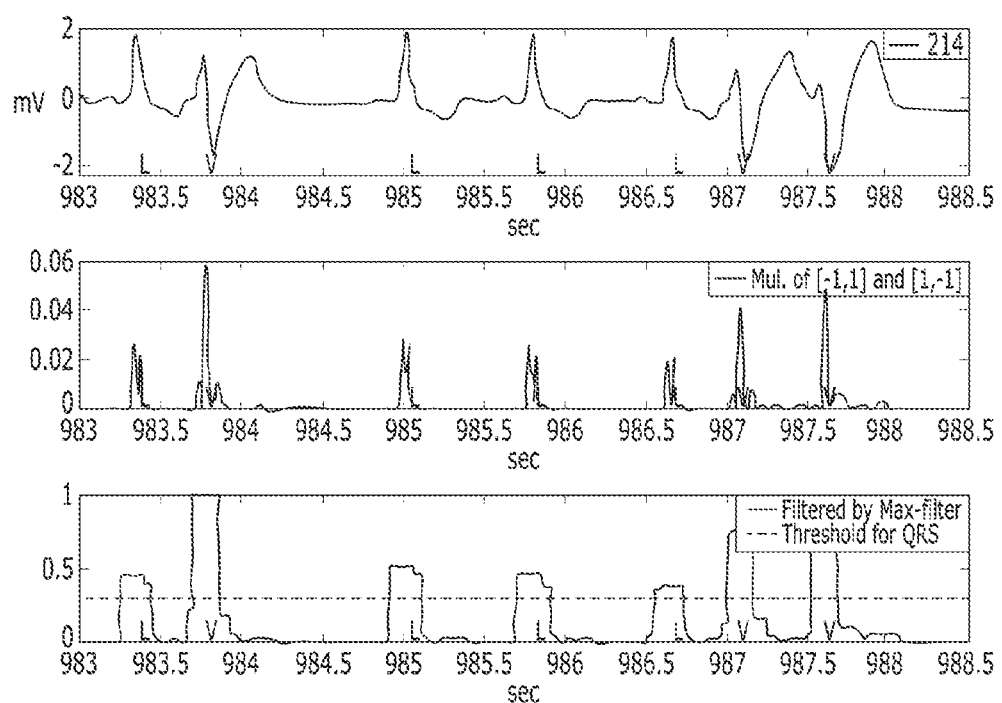
Figure 12E:
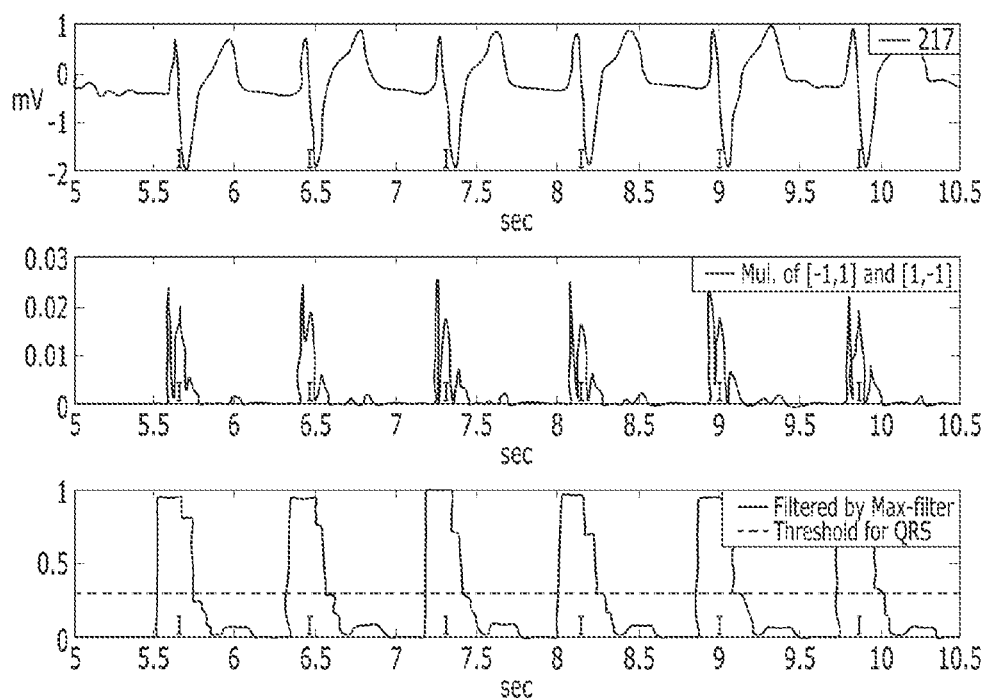

As shown in FIG. 11, the position $r_L$ of an R-peak found in a local signal interval corresponding to the candidate QRS interval is compared to an offset value and then is computed using the R-peak position $r_W$ in the sliding window as expressed in Equation 8.

$$r_W = \begin{cases} j - (\text{offset} + 1) - r_L, & \text{if } r_L < \text{offest} \\ j + r_L - \text{offset}, & \text{else}(r_L \le \text{offest}) \end{cases} \quad \text{[Equation 8]}$$

where j is a point position in a sliding window, and W and L are local signals corresponding to a sliding window and a candidate QRS.

Also, an R-peak position in an original signal is computed by step size s as expressed in Equation 9.

$$r = r_W + (s-1) \quad \text{[Equation 9]}$$

FIG. 12A through FIG. 12E show a QRS detection result for the sections of records 108, 111, 118, 217, and 214 of the MIT-BIH arrhythmia database according to an embodiment of the present invention.

FIG. 12A through FIG. 12E show a QRS detection result obtained by applying a pair of derivative filters and a max-filter to records 108, 111, 118, 217, and 214 in the MIT-BIH arrhythmia database.

N, L, R, /, and V represent NSR, LBBB, RBBB, Paced, and PVC beat.

According to an embodiment of the present invention, MIT-BIH ECG signals are filtered by a low-frequency bandpass filter with a cutoff frequency of 40 Hz.

The section of record 108 is an unusual NSR rhythm including a large P-wave and inverse QRS.

The section of record 111 is an LBBB rhythm including notched QRS and a large T-wave.

The section of record 118 is an RBBB rhythm including a modified P-wave and an inverse T-wave.

The section of record 217 is a paced rhythm including a deep S-wave and a large T-wave, and the section of record 214 is a complex rhythm having both LBBB and PVC beats.

In the product result of the pair of derivative filters, a large P-wave and a large T-wave are suppressed while a QRS complex is improved.

Also, the QRS complex may be detected by applying a constant threshold to a normalized max-filter result for the product result of the pair of derivative filters.

Figure 13:
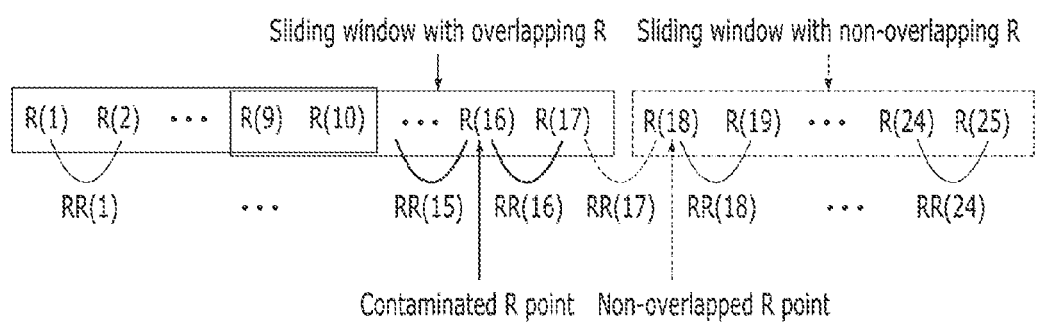
FIG. 13 shows R-R exclusion with low reliability according to an embodiment of the present invention.

FIG. 13 shows R-R exclusion with low reliability according to an embodiment of the present invention.

The reliability of a detected R-point is considered when determining whether R is present in a noise region or whether the first R in the current sliding window overlaps R in the previous sliding window.

As shown in FIG. 13, R(n) represents the position of an R-point that is detected for the nth time in the entire ECG signal.

When R(16) is an unreliable R-point detected in the noise region, then RR(15) and RR(16) calculated based on R(16) are also unreliable and are excluded from HRV analysis.

When R(18) is an R-point detected in the current sliding window for the first time and does not overlap R-points in the previous sliding window, the R-points detected in the sliding windows lack continuity.

Accordingly, RR(17) calculated from R(18) is not reliable and is excluded from the HR.); analysis.

However, R(18) and R(19) are guaranteed to have continuity, so RR(18) is a reliable R-R interval.

Figure 14:
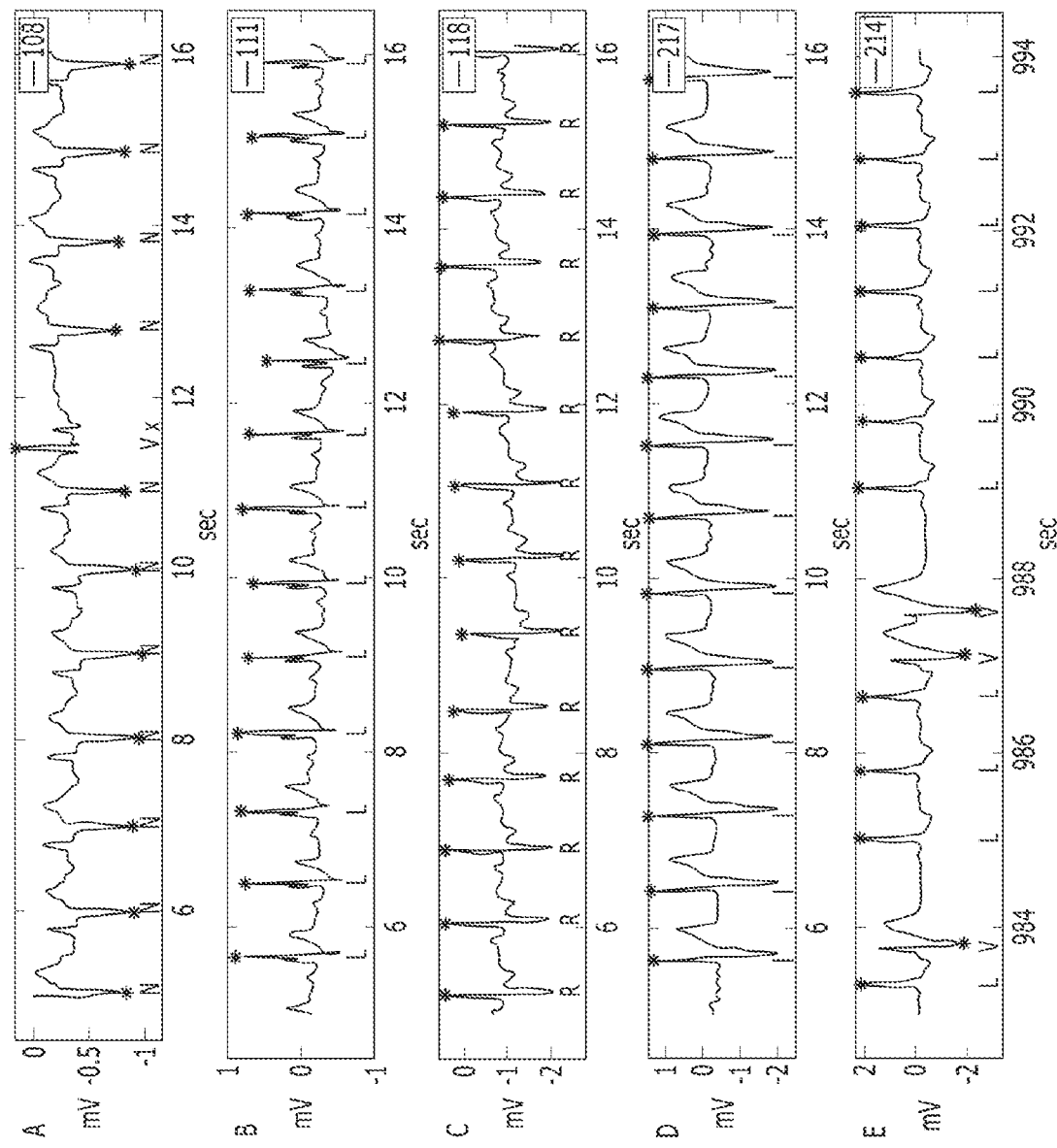
FIG. 14 shows an R-point detection result for records 108, 111, 118, 217, and 214 in the MIT-BIH arrhythmia database according to an embodiment of the present invention.

FIG. 14 shows an R-point detection result for records 108, 111, 118, 217, and 214 in the MIT-BIH arrhythmia database according to an embodiment of the present invention.

It can be seen that the positions of PVC and inverse QRS are well detected although the section of record 108 includes a large P-wave and the inverse QRS.

x denotes a non-conducted P-wave (blocked APB).

It can be seen that periodic R-points are well detected although the section of record 111 includes a notched QRS and a relatively large T-wave.

The R-detection of the section of record 118 is very easy compared to other signal sections.

It can be seen that positive R-points are well detected although the section of record 217 includes a deep S-wave and a large T-wave.

According to an embodiment of the present invention, it can be seen that a PVC beat including a positive R-point and a large T-wave is well detected in the section of record 214.

According to an embodiment of the present invention, it is possible to increase robustness against noise in QRS detection by using a pair of derivative filters and also to improve analysis reliability by excluding QRS information contaminated with noise from an R-R interval analysis. Thus, it is possible to monitor the ECG state of a patient with arrhythmia or suspected arrhythmia in real time and prevent heart disease incidents.

Meanwhile, the method of detecting ventricular depolarization of an electrocardiogram according to an embodiment of the present invention may be implemented in a computer system or recorded on a recording medium. The computer system may include at least one processor, memory, user input device, data communication bus, user output device, and storage, The above-described elements perform data communication through the data communication bus.

The computer system may further include a network interface coupled to a network. The processor may be a central processing unit (CPU) or a semiconductor device for processing instructions stored in a memory and/or a storage.

The memory and storage may include various types of volatile or non-volatile storage media. For example, the memory may include a read-only memory (ROM) and a random access memory (RAM).

Accordingly, the method of detecting ventricular depolarization of an electrocardiogram according to an embodiment of the present invention may be implemented as a computer-executable method. When the method of detecting ventricular depolarization of an electrocardiogram according to an embodiment of the present invention performed by a computer apparatus, computer-readable instructions may perform the detection method according to the present invention.

Meanwhile, the method of detecting ventricular depolarization of an electrocardiogram according to the present invention may be implemented as computer-readable code on a computer-readable recording medium. The computer-readable recording medium includes any type of recording medium in which data that can be decrypted by a computer system is stored. For example, the computer-readable recording medium may include a ROM, a RAM, a magnetic tape, a magnetic disk, a flash memory, an optical data storage device, and the like. Further, the computer-readable recording medium can be stored and carried out as codes that are distributed in a computer system connected to a computer network and that are readable in a distributed manner.

According to an embodiment of the present invention, it is possible to increase robustness against noise in QRS detection by using a pair of derivative titters and also to improve analysis reliability by excluding QRS information contaminated with noise from an R-R interval analysis. Thus, it is possible to monitor the ECG state of a patient with arrhythmia or suspected arrhythmia in real time and prevent heart disease incidents.

Advantageous effects of the present invention are not limited to the aforementioned effects, and other effects not described herein will be clearly understood by those skilled in the art from the above description.

The present invention has been described above with respect to embodiments thereof. Those skilled in the art should understand that various changes in form and details may be made therein without departing from the essential characteristics of the present invention. Therefore, the embodiments described herein should be considered from an illustrative aspect rather than from a restrictive aspect. The scope of the present invention should be defined not by the detailed description. but by the appended claims, and all differences falling within a scope equivalent to the claims should be construed as being encompassed by the present invention.

Figure 15:
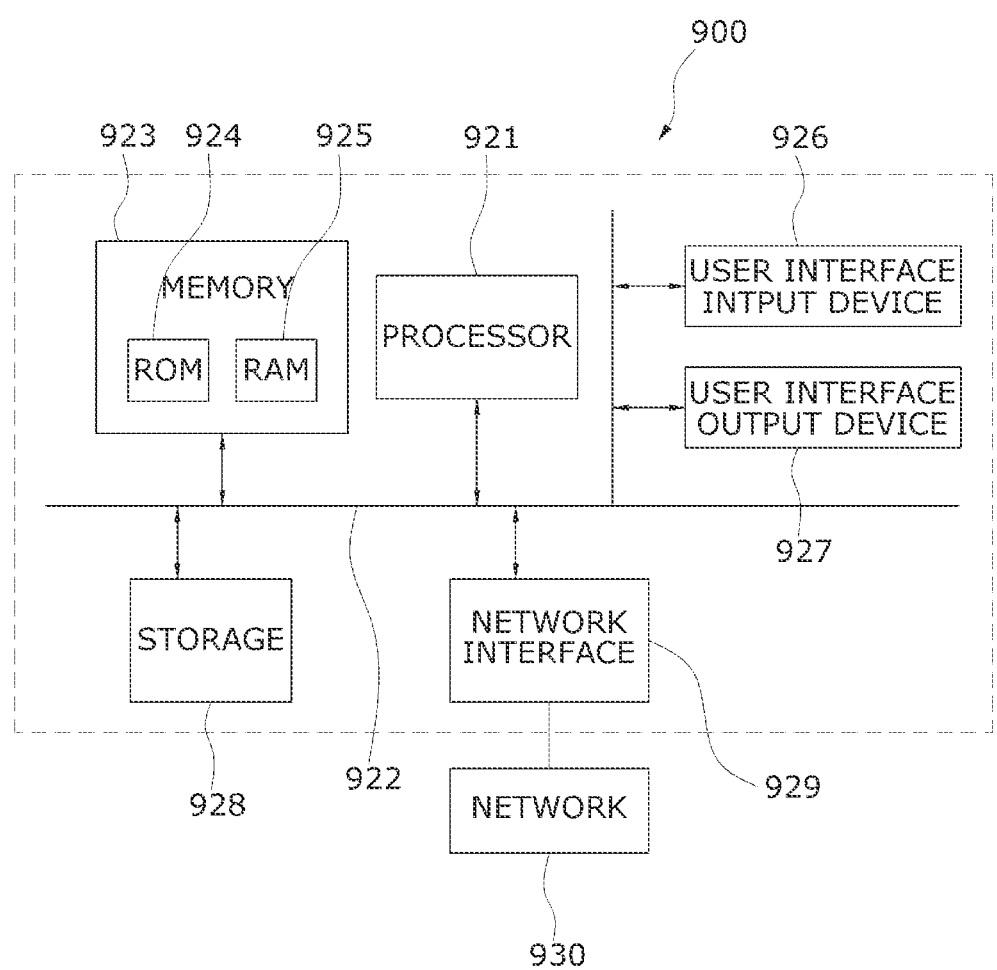
FIG. 15 is a view illustrating an example of a computer system in which a method according to an embodiment of the present invention is performed.

The method according to an embodiment of the present invention may be implemented in a computer system or may be recorded in a recording medium. FIG. 15 illustrates a simple embodiment of a computer system. As illustrated, the computer system may include one or more processors 921, a memory 923, a user input device 926, a data communication bus 922, a user output device 927, a storage 928, and the like. These components perform data communication through the data communication bus 922.

Also, the computer system may further include a network interface 929 coupled to a network. The processor 921 may be a central processing unit (CPU) or a semiconductor device that processes a command stored in the memory 923 and/or the storage 928.

The memory 923 and the storage 928 may include various types of volatile or non-volatile storage mediums. For example, the memory 923 may include a RUM 924 and a RAM 925.

Thus, the method according to an embodiment of the present invention may be implemented as a method that can be executable in the computer system.

When the method according to an embodiment of the present invention is performed in the computer system, computer-readable commands may perform the producing method according to the present invention.

The method according to the present invention may also be embodied as computer-readable codes on a computer-readable recording medium. The computer-readable recording medium is any data storage device that may store data which may be thereafter read by a computer system. Examples of the computer-readable recording medium include read-only memory (ROM), random access memory (RAM), CD-ROMs, magnetic tapes, floppy disks, and optical data storage devices. The computer-readable recording medium may also be distributed over network coupled computer systems so that the computer-readable code may be stored and executed in a distributed fashion.

The technical objectives of the present invention are not limited to the above, and other objectives may become apparent to those of ordinary skill in the art based on the specification.

Although the present invention has been described with reference to the embodiments, a person of ordinary skill in the art should appreciate that various modifications, equivalents, and other embodiments are possible without departing from the scope and spirit of the present invention. Therefore, the embodiments disclosed above should be construed as being illustrative rather than limiting the present invention, The scope of the present invention is not defined by the above embodiments but by the appended claims of the present invention, and the present invention is to cover all modifications, equivalents, and alternatives falling within the spirit and scope of the present invention, The components described in the example embodiments may be implemented by hardware components including, for example, at least one digital signal processor (DSP), a processor, a controller, an application-specific integrated. circuit (ASIC), a programmable logic element, such as an FPGA, other electronic devices, or combinations thereof. At least some of the functions or the processes described in the example embodiments may be implemented by software, and the software may be recorded on a recording medium. The components, the functions, and the processes described in the example embodiments may be implemented by a combination of hardware and software.

The method according to example embodiments may be embodied as a program that is executable by a computer, and may be implemented as various recording media such as a magnetic storage medium, an optical reading medium, and a digital storage medium.

Various techniques described herein may be implemented as electronic circuitry, or as computer hardware, firmware, software, or combinations thereof. The techniques may be implemented as a computer program product, i.e., a computer program tangibly embodied in an information carrier, e.g., in a machine-readable storage device (for example, a computer-readable medium) or in a propagated signal for processing by, or to control an operation of a data processing apparatus, e.g., a programmable processor, a computer, or multiple computers. A computer program(s) may be written in any form of a programming language, including compiled or interpreted languages and may be deployed in any form including a stand-alone program or a module, a component, a subroutine, or other units suitable for use in a computing environment. A computer program may be deployed to be executed on one computer or on multiple computers at one site or distributed across multiple sites and interconnected by a communication network.

Processors suitable for execution of a computer program include, by way of example, both general and special purpose microprocessors, and any one or more processors of any kind of digital computer. Generally, a processor will receive instructions and data from a read-only memory or a random access memory or both. Elements of a computer may include at least one processor to execute instructions and one or more memory devices to store instructions and data. Generally, a computer will also include or be coupled to receive data from, transfer data to, or perform both on one or more mass storage devices to store data, e.g., magnetic, magneto-optical disks, or optical disks. Examples of information carriers suitable for embodying computer program instructions and data include semiconductor memory devices, for example, magnetic media such as a hard disk, a floppy disk, and a magnetic tape, optical media such as a compact disk read only memory (CD-ROM), a digital video disk (DVD), etc. and magneto-optical media such as a floptical disk, and a read only memory (ROM), a random access memory (RAM), a flash memory, an. erasable programmable ROM (EPROM), and an electrically erasable programmable ROM (EEPROM) and. any other known computer readable medium. A processor and a memory may be supplemented by, or integrated into, a special purpose logic circuit.

The processor may run an operating system (OS) and one or more software applications that run on the OS. The processor device also may access, store, manipulate, process, and create data in response to execution of the software. For purpose of simplicity, the description of a processor device is used as singular; however, one skilled in the art will be appreciated that a processor device may include multiple processing elements and/or multiple types of processing elements. For example, a processor device may include multiple processors or a processor and. a controller. In addition, different processing configurations are possible, such as parallel processors.

Also, non-transitory computer-readable media may be any available media that may be accessed by a computer, and may include both computer storage media and transmission media.

The present specification includes details of a number of specific implements, but it should be understood that the details do not limit any invention or what is claimable in the specification but rather describe features of the specific example embodiment. Features described in the specification in the context of individual example embodiments may be implemented as a combination in a single example embodiment. In contrast, various features described in the specification in the context of a single example embodiment may be implemented in multiple example embodiments individually or in an appropriate sub-combination. Furthermore, the features may operate in a specific combination and may be initially described as claimed in the combination, but one or more features may be excluded from the claimed combination in some cases, and the claimed combination may be changed into a sub-combination or a modification of a sub-combination.

Similarly, even though operations are described in a specific order on the drawings, it should not be understood as the operations needing to be performed in the specific order or in sequence to obtain desired results or as all the operations needing to be performed. In a specific case, multitasking and parallel processing may be advantageous, In addition, it should not be understood as requiring a separation of various apparatus components in the above described example embodiments in all example embodiments, and it should be understood that the above-described program components and apparatuses may be incorporated into a single software product or may be packaged in multiple software products.

It should be understood that the example embodiments disclosed herein are merely illustrative and are not intended to limit the scope of the invention. It will be apparent to one of ordinary skill iii the art that various modifications of the example embodiments may be made without departing from the spirit and scope of the claims and their equivalents.

What is claimed is:

1. A method of detecting ventricular depolarization of an electrocardiogram (ECG), the method comprising:
receiving an ECG signal using an input unit;
storing computer executable program code in non-transitory computer readable storage media, the computer executable program code for detecting R and ventricular depolarization using the ECG signal;
using at least one processor that processes the computer executable program code stored in the non-transitory computer readable storage media, the computer executable program code comprising:
(a) detection program code that detects a QRS interval and an R-peak by applying a pair of derivative filters and a max-filter to the received ECG signal;
(b) detection program code that detects a noise interval and an R-peak in the noise interval; and (c) setting program code that sets a candidate of an R-R interval and modifying program code that modifies the R-R interval in consideration of noise, wherein (a) comprises detecting a QRS feature using a pair of first-order derivative filters for a rising derivative filter and a falling derivative filter.

2. The method of claim 1, wherein (a) comprises detecting the QRS feature by multiplying results of applying the pair of first-order derivative filters.

3. The method of claim 1, wherein (a) comprises applying the max-filter to extend a QRS candidate interval and detecting a QRS interval using a threshold.

4. A method of detecting ventricular depolarization of an electrocardiogram (ECG), the method comprising:

receiving an ECG signal using an input unit;

storing computer executable program code in non-transitory computer readable storage media, the computer executable program code for detecting R and ventricular depolarization using the ECG signal;

using at least one processor that processes the computer executable program code stored in the non-transitory computer readable storage media, the computer executable program code comprising:

(a) detection program code that detects a QRS interval and an R-peak by applying a pair of derivative filters and a max-filter to the received ECG signal;

(b) detection program code that detects a noise interval and an R-peak in the noise interval; and (c) setting program code that sets a candidate of an R-R interval and modifying program code that modifies the R-R interval in consideration of noise, wherein (b) comprises classifying a noise region from the ECG signal using a vertical histogram.

5. The method of claim 4, wherein (c) comprises excluding preceding and following R-R intervals related to the R-peak detected in the noise region from analysis.

6. The method of claim 4, wherein (c) comprises determining whether an initial R in a current sliding window overlaps R in a previous sliding window and excluding an R-R interval lacking continuity between the sliding windows from analysis.

* * * * *